(12) United States Patent
Lee et al.

(10) Patent No.: US 7,223,555 B2
(45) Date of Patent: May 29, 2007

(54) METHOD FOR DETECTING ELEVATED ACTIVITY OF OXIDASES IN INSECTS

(75) Inventors: Han Lim Lee, Selangor (MY); Wasi Ahmad Nazni, Selangor (MY)

(73) Assignee: Institute for Medical Research, Wilayah Persekutuan (MY)

( * ) Notice: Subject to any disclaimer, the term of this patent is extended or adjusted under 35 U.S.C. 154(b) by 430 days.

(21) Appl. No.: 10/321,723

(22) Filed: Dec. 18, 2002

(65) Prior Publication Data

US 2004/0101925 A1 May 27, 2004

(30) Foreign Application Priority Data

Nov. 26, 2002 (MY) ............................. PI 20024414

(51) Int. Cl.
*C12Q 1/26* (2006.01)
(52) U.S. Cl. ........................... 435/25; 435/29; 435/348
(58) Field of Classification Search .................. 435/25, 435/4, 975, 29, 348
See application file for complete search history.

(56) References Cited

U.S. PATENT DOCUMENTS 5,871,939 A * 2/1999 Trowell et al. ............ 435/7.21
2003/0100025 A1 * 5/2003 O'Connor et al. ........... 435/7.2
2004/0101925 A1 * 5/2004 Lee et al. .................... 435/25

OTHER PUBLICATIONS

Vulule et al, Medical & Vetinary Entomology, v. 13(3), p. 239, Sep. 1999, (Abstract Only).*

* cited by examiner

*Primary Examiner*—Ralph Gitomer
(74) *Attorney, Agent, or Firm*—Lowe Hauptman & Berner LLP

(57) ABSTRACT

A method for checking for elevated activity of mixed-function oxidases using a single insect, includes homogenizing a single insect in an acid pH buffer, preferably by grinding it in a small tube, such as an Eppendorf tube, with a pestle, adding a buffered tetramethylbenzidine solution as substrate, adding hydrogen peroxide as oxidant, and checking the blue coloration, the intensity of which indicates the degree of elevated mixed function oxidase activity. The invention also provides a test kit for use in the method which comprises separate containers of: I. an acid pH buffer, preferably an acid buffer about pH5 II. tetramethylbenzidine III. a solvent for tetramethylbenzidine, preferably methanol, and IV. hydrogen peroxide.

8 Claims, No Drawings

METHOD FOR DETECTING ELEVATED ACTIVITY OF OXIDASES IN INSECTS

This invention relates to a method and test kit for determining insect resistance to insecticides and more particularly provides a method and test kit for field use for determining insect resistance to pyrethroid based insecticides.

BACKGROUND TO THE INVENTION

Chemical insecticides remain as the most important agents for the control of vector-borne diseases such as malaria, dengue, filariasis etc. Countless deaths from these diseases have been spared since the introduction of the first synthetic insecticide, DDT in the 1940's. Prolonged use of insecticides has however, induced the development of resistance in the vectors, primarily insects, that carry such diseases, which renders them less effective in combating the vectors and thus the diseases that they spread. Resistance detection is mainly based on the World Health Organisation (WHO) standard test procedures which, among other things, are not user-friendly, use test kits of short shelf life and need skilled manpower to conduct the tests and interpret the test results. As a result, very often little is known of the susceptibility status of many insect vectors, which tends to affect the outcomes of control programmes.

The development of rapid field test kits would be a major breakthrough in the control of vector-borne diseases.

In general, the biochemical basis of resistance is due to 3 mechanisms:
1) increased level of non-specific esterases targeted against organophosphates and carbamates;
2) elevated activity of mixed-function oxidases against pyrethroids; and
3) non-susceptability of acetylcholine esterase against organophosphates and carbamates.

SUMMARY OF THE INVENTION

This invention provides a method and test kit for determining elevated activity of mixed-function oxidases in insects using a single insect that is quick and easy to use and produces results that are very simple to interpret.

According to the invention the test kit comprises a container containing separate containers of:
I. an acid pH buffer
II. tetramethylbenzidine
III. a solvent capable of dissolving tetramethylbenzidine and
IV. hydrogen peroxide For field use the kit will also contain the equipment for carrying out the test, for example mixing containers, test tubes, for example Eppendorf tubes, a pipette and a micro-assay plate and, usually, a colour chart.

The buffered pH is preferably 4 to 6, more preferably about 5.

The pH buffer is preferably sodium acetate.

The solvent is preferably absolute methanol.

The hydrogen peroxide is preferably used as a 3% w/w aqueous solution.

The method of the invention comprises homogenizing a single insect in the buffer, preferably by grinding it in a small tube, such as an Eppendorf tube, with a pestle, adding buffered tetramethylbenzidine solution as substrate, adding hydrogen peroxide as oxidant, and checking the blue coloration, the intensity of which indicates the degree elevated mixed function oxidase activity, and hence resistance to pyrethroid based insecticides.

The coloration for a non-resistant insect is at most very faint and increases to dark blue as the degree of resistance increases.

The degree of coloration can be estimated by eye, by comparison with a colour chart or, if more accurate results are needed, by scanning with an immuno-assay reader at 630 nm.

The invention has the advantage of being the first test kit available for testing for elevated activity of mixed-function oxidases that requires only a single insect for testing and that is used in a method that gives rapid test results that are obtainable virtually instantaneously and which can be read visually and calorimetrically without equipment. The test kits and method require less skilled manpower and are easy to use without special training. Moreover, the kits have a long shelf life and are stable for weeks at room temperature Use of the kit will:
1. considerably simplify resistance detection
2. ensure that chemical insecticides used to control pests and disease vectors are effective and hence save lives, cost and manpower
3. allow constant and regular monitoring of the susceptibility of target insects and
4. assist in the design of new control agents, countermeasures and understanding of the mode of action of insecticides.

DESCRIPTION OF PREFERRED EMBODIMENT

Five bottles were prepared containing, respectively 10 ml of sodium acetate buffer (pH 5), 2.5 ml of absolute methanol, 5 mg tetramethylbenzidine, 7.5 ml of sodium acetate buffer (pH 5) and 5 ml hydrogen peroxide (3%)

To carry out the test, the absolute methanol is poured into the tetramethylbenzidine and shaken to dissolve the tetramethylbenzidine completely and the resulting solution is buffered with the 7.5 ml of sodium acetate buffer. A single mosquito is homogenized in one drop of the buffer in an Eppendorf tube using a pestle and further diluted with buffer to the 1 ml mark on the Eppendorf tube. Two drops of the homogenisate are dropped into each well of a micro-assay plate followed by four drops of the tetamethylbenzidine solution and one drop of the hydrogen peroxide.

The results were assessed by eye scoring, by colour checking against a calibrated colour chart or by scanning using an immunoassay reader at 630 nm.

The invention claimed is:

1. A method for detecting elevated activity of mixed-function oxidases in insects, comprising:
   homogenizing a single insect in an acid pH buffer,
   adding acid pH-buffered tetramethylbenzidine solution as substrate,
   adding hydrogen peroxide as an oxidant, and thereafter detecting blue coloration, and
   determining elevated mixed function oxidase activity by correlating the detected blue coloration with predetermined colorations on a color chart.

2. The method of claim 1, wherein the buffer is a pH 4 to 6 buffer.

3. The method of claim 2, wherein the buffer is a pH 5 buffer.

4. The method of claim 2, wherein the buffer is sodium acetate.

5. The method of claim 1, wherein the solvent is absolute methanol.

6. The method of claim 1, wherein the hydrogen peroxide is a 3% w/w aqueous solution.

7. The method of claim 1, wherein the detection of blue coloration is conducted visually.

8. The method of claim 1, wherein the detection of blue coloration is conducted by immunoassay reader at 630 nm.

* * * * *